United States Patent [19]

Dorworth

[11] Patent Number: 5,340,578
[45] Date of Patent: Aug. 23, 1994

[54] **METHOD FOR CONTROLLING RED ALDER USING *NECTRIA DITISSIMA* ATCC 74260**

[75] Inventor: Charles E. Dorworth, Victoria, Canada

[73] Assignee: Forestry Canada, Hull, Canada

[21] Appl. No.: 87,005

[22] Filed: Jul. 7, 1993

[51] Int. Cl.$^5$ .................. A01N 63/00; A61K 37/00; C12N 1/00; C12N 1/19
[52] U.S. Cl. .................... 504/117; 435/911; 435/254.1
[58] Field of Search .................. 424/93 Q; 427/93 Q

[56] References Cited

PUBLICATIONS

Dorworth (1990) Ministry of Forestry, FRI Bulletin, 155, 116–119.
Flack et al (1977) Trans Br. Mycol Soc., 68(2), 185–192.
P. Capretti and C. E. Dorworth (1989) Eur. J. For Path, 19, 407–413.
Sieber et al (1991) Can J Bot, 69, 407–411.
Dorworth (1979) Phytopathology, 69(3), 298–300.
Seiber et al (1989) Can J of Plant Pathology, 11(2), 198.

*Primary Examiner*—David M. Naff
*Assistant Examiner*—Jeffrey J. Sevingny
*Attorney, Agent, or Firm*—George A. Seaby

[57] ABSTRACT

The control of weed trees in reforestation areas is expensive chemical herbicides and falling into disfavour and ultimately may be banned completely. Moreover, the application of herbicides is labor intensive. A simple, effective solution to the problem is to use a biological method of controlling weed trees in which a wooden charge containing a fungus capable of killing the trees is injected into the trees. Preferably the fungus is indigenous to the area of the trees being treated. Red Alder can be effectively controlled using the fungus *Nectria ditissima*.

7 Claims, 1 Drawing Sheet

METHOD FOR CONTROLLING RED ALDER USING *NECTRIA DITISSIMA* ATCC 74260

BACKGROUND OF THE INVENTION

1. Field of the Invention

This invention relates to a method, apparatus and product for biologically controlling weed trees.

More specifically, the invention relates to the biological control of red alder (*Alnus rubra* Bong) and similar weeds using a fungus of the genus Nectria, preferably *Nectria ditissima*.

2. Discussion of the Prior Art

The control of weed trees such as red alder in reforestation areas is expensive in terms of weeding costs and lost growth potential of forest areas. Chemical herbicides are used to remove the majority of alders from 15 to 40 year old conifer plantations in the Pacific Northwest of the United States and contiguous areas of Canada. For example, more than 90% of the backlog brushland clearing in British Columbia is accomplished with Vision (a trademark of Monsanto Corporation for glyphosate). Public perception of chemical herbicides is negative and there is a distinct possibility that the use of major herbicides will ultimately be banned. In fact, herbicides are presently banned on public lands in several areas including Alberta and Quebec, Canada, U.S. Forest Service (Region 3), Sweden and Switzerland. Loss of such chemicals in backlog operations and plantation clearing will present foresters with a major problem and forestry firms with substantially higher expenses because of bush clearance and replant costs. Moreover, the application of presently used herbicides is labor intensive, requiring workers to walk through plantations, remove a strip of bark around each weed tree, and paint a herbicide onto and into the wounds. The circumference of older trees is often irregular and the task may require considerable time. The rapid killing of trees using chemicals results in rapid degradation of the root nodules, which often contain a surfeit of fixed nitrogen, with consequent rapid oxidation of nitrogen. The nitrogen forms gaseous oxide gases which dissipate, becoming unavailable for replenishment of already scarce forest nitrogen stocks.

GENERAL DESCRIPTION OF THE INVENTION

An object of the present invention is to provide a solution to the problems involved in the use of chemical herbicides in the form of a biological method of controlling red alder. Of course, the basic method is equally applicable to other weed trees.

Another object of the invention is to provide a method of the above described type which while controlling weed trees, does not harm conifers or other desired vegetation.

The above objects are met by a biological method of controlling a weed tree comprising the step of injecting a wooden charge containing a fungus capable of killing the tree over an extended period of time into the tree.

The above described method is carried out using a device for injecting a wooden charge into a weed tree, wherein the charge is in the form of an elongated body having tapered ends, comprising elongated, tubular barrel means having a closed end and an open end for receiving a plurality of axially aligned charges; hammer means on said closed end of said barrel means for forming a recess in a tree approximating the shape of the charge; gate means normally closing said open end of said barrel means; handle means on said open end of the barrel means for moving said gate means between the barrel closing and open positions; and spring means in the closed end of said barrel means for biasing any charges in the barrel means against said gate means, whereby opening of the gate means will permit the discharge of a charge from said barrel means.

The charge referred to in describing the device for carrying out the method includes an elongated wooden body having tapered ends to facilitate insertion of the charge into a recess in the tree, and an impregnant of a fungus capable of killing the tree in said body.

The process described herein is not intended to kill trees quickly, but rather over a period of several years. The killing of forest intragrowths of red alder over a five year period will release nitrogen produced by the symbiosis of alder and the bacterium Frankia slowly such that the nitrogen is not volatilized by massive localized growth of bacteria and more becomes available for the developing conifer forest. This environmentally friendly method of removing red alder from conifer plantations reduces competition to conifers and decreases the time from newly planted seedling to harvestable tree. Stated in another manner, the method results in larger and more valuable trees than could be produced in the same time frame if alder competition was not reduced or eliminated.

In the specific embodiment of the method, the specific biological control agent (*Nectria ditissima* Tul.) used is a native fungus which is far more effective than other fungi tested once inoculated into a tree. The fungus is successfully inoculated into trees using the device and charge described hereinafter in greater detail. The fungus *Nectria ditissima* Tul., and the particular isolate PFC-082 (which has been deposited under ATCC No. 74260, under the terms of the Budapest Treaty and the accessibility of which will be irrevocably and without restriction or condition released to the public) were chosen after extensive testing from a number of isolates. The isolate is highly virulent as demonstrated in records of tree mortality (not included) and in consistency of successful inoculation and extent of tissue damage (Table 1 below), both of which are significantly different from the control.

In greater detail, the method of the invention involves the following two steps:

As a first or preliminary step, fungus is incubated aseptically on 0.5" diameter wooden plugs or charges having tapered ends and impregnated with nutrients (possibly antioxidants and antibacterial agents - as individual situations dictate).

After 2–3 months of fungus growth the charges are inserted into the stems of alders using the device described herein or a similar device.

In preliminary research, alders of 15 to 40 cm diameter were inoculated with a variety of fungi in the final test of a five year series. The results are set out in Table 1, which provides an indication of canker or killed tissue length and the percentage of red alder stems cankered two years after stem inoculation with a variety of biocontrol agents. The isolate numbers in the lefthand column are the inventor's designations.

TABLE 1

| Isolate No. | Name | Diam. (cm) | Canker length (cm) | % Stems cankered |
|---|---|---|---|---|
| PFC-011 | *Melanconis* | 15–20 | 40 | 50 |

TABLE 1-continued

| Isolate No. | Name | Diam. (cm) | Canker length (cm) | % Stems cankered |
|---|---|---|---|---|
| | marginalis (Peck.) Wehm. | 20–25 | 3 | 50 |
| | | 25–30 | 2 | 33 |
| | | 30–35 | 10 | 33 |
| | | 35–40 | 1 | 17 |
| PFC-012 | Melanconis marginalis (Peck.) Wehm. | 15–20 | 19 | 50 |
| | | 20–25 | 7 | 50 |
| | | 25–30 | 26 | 80 |
| | | 35–40 | 1 | 17 |
| PFC-FC-1240 | Didymosphaeria oregonensis Goodling | 15–20 | 28 | 40 |
| | | 20–25 | 10 | 50 |
| | | 25–30 | 3 | 20 |
| | | 30–35 | 5 | 33 |
| | | 35–40 | 0 | 0 |
| PFC-043 | Melanconis alni Tul. | 15–20 | 21 | 100 |
| | | 20–25 | 28 | 100 |
| | | 25–30 | 10 | 40 |
| | | 30–35 | 2 | 17 |
| | | 35–40 | 5 | 17 |
| PFC-054 | Melanconis alni Tul. | 15–20 | 57 | 75 |
| | | 20–25 | 36 | 50 |
| | | 25–30 | 11 | 67 |
| | | 30–35 | 4 | 17 |
| | | 35–40 | 0 | 0 |
| PFC-065 | Nectria ditissima Tul. | 15–20 | 12 | 67 |
| | | 20–25 | 5 | 50 |
| | | 25–30 | 17 | 50 |
| | | 30–35 | 9 | 33 |
| | | 35–40 | 4 | 17 |
| PFC-075 | Phomopsis sp. | 15–20 | 18 | 100 |
| | | 20–25 | 10 | 50 |
| | | 25–30 | 10 | 50 |
| | | 30–35 | 10 | 50 |
| | | 35–40 | 14 | 50 |
| PFC-082 | Nectria sp. | 15–20 | 70 | 60 |
| | | 20–25 | 60 | 100 |
| | | 25–30 | 61 | 100 |
| | | 30–35 | 65 | 100 |
| | | 35–40 | 50 | 100 |
| PFC-085 | Valsna alni Peck. | 15–20 | 11 | 33 |
| | | 20–25 | 8 | 50 |
| | | 25–30 | 11 | 67 |
| | | 30–35 | 13 | 40 |
| | | 35–40 | 2 | 33 |
| PFC-088 | Hypoxylon mammatum (Wahl.) J. H. Miller | 15–20 | 19 | 80 |
| | | 20–25 | 7 | 50 |
| | | 25–30 | 19 | 60 |
| | | 30–35 | 6 | 50 |
| | | 35–40 | 0 | 0 |
| PFC-090 | Xylaria hypoxylon | 15–20 | 4 | 50 |
| | | 20–25 | 4 | 33 |
| | | 25–30 | 28 | 50 |
| | | 30–35 | 9 | 17 |
| | | 35–40 | 2 | 17 |

It will be noted that the rate of mortality of the trees is inversely proportional to stem diameter (preliminary data), with cankers (strips of killed tissues) of 60 to 90 cm length developed in the first 2 years and cankers as long as 2 meters developed by the end of 2.5 years, with scattered mortality at that time. The method is not intended for use with stems < 10 cm diam. nor > than 40 cm. It is intended that this method of control fit into an overall forest management - integrated pest management (IPM) plan, integrated as one component of the standard per-commercial thinning and sanitation procedures applied at 10 to 40 years of the tree age, with alder death occurring over a 3 to 5 year period. The results found in Table 1 indicate that isolate PFC-082 is the fungus which achieves both a consistent high degree of infection and acceptable canker length in red alder stems.

BRIEF DESCRIPTION OF THE DRAWINGS

The device and charge used to carry out the inoculation step of the method will be described with reference to the accompanying drawing, wherein.

DESCRIPTION OF PREFERRED EMBODIMENT

Figure 1:
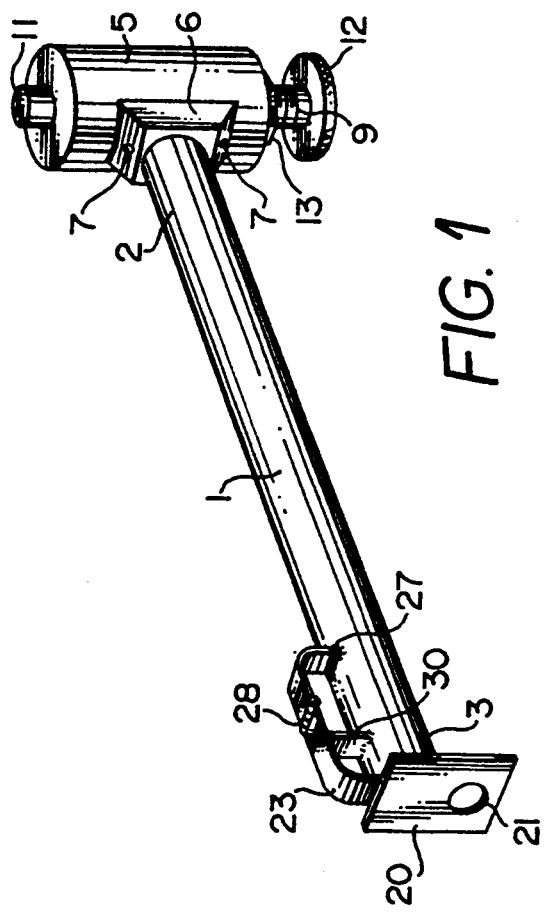
FIG. 1 is a schematic, perspective view of a device for inoculating a tree.

Referring to the drawing, the device for inoculating a tree, i.e. placing a charge in a tree includes an elongated tubular barrel 1, with a closed end 2 and an open end 3. A cylindrical hammer body 5 is mounted on the closed end 2 of the barrel 1 by means of a block 6 on such closed end and a pair of screws 7. An elongated rod 9 with a threaded end 10 extends through the body 5. The threaded end 10 of the rod 9 engages threads in the body 5 for adjusting the length of the head or other end 11 extending out of the body 5. The rod 9 is rotated by a knurled head 12 on the threaded end 10 of the rod. The rod is fixed in one position by a nut 13, i.e. the nut limits movement of the threaded end 10 of the rod into the body 5. When the head 11 of the rod 9 is hammered against a tree trunk, a cylindrical recess is produced in the trunk.

Figure 2:
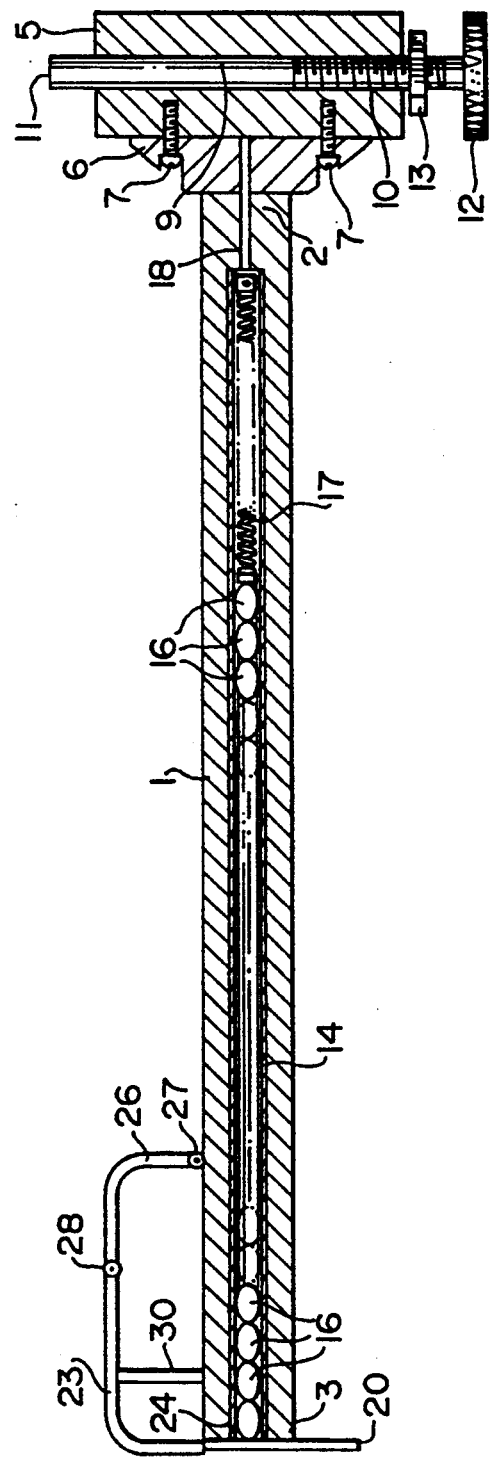
FIG. 2 is a longitudinal sectional view of the device of FIG. 1.

The barrel 1 is adapted to receive a magazine 14 defined by a hard plastic tube. The magazine 14 is loaded with wooden plugs or charges 16 previously colonized by a suitable fungus. A spring 17 in one end of the magazine 14 biases the charges 16 towards the open end 3 of the barrel 1. A small hole 18 in the closed end 2 of the barrel 1 permits adjustment of the spring tension. The open end 3 of the barrel 1 is normally closed by a gate 20, which includes an opening 21 (FIG. 1) in the bottom end thereof. The gate 20 is carried by one end of a handle 23 for sliding between the closed position (FIGS. 1 and 2) and an open position in which the opening 21 is aligned with the open end 24 of the magazine 14. A dovetail or other slide (not shown) can be provided between the end 3 of the barrel 1 and the gate 20 for maintaining the gate against the such end of the barrel. The handle 23 is generally C-shaped, the rear end 26 thereof being pivotally connected to the barrel 1 by a hinge 27. A second hinge 28 is provided in the top of the handle, the hinges permitting pivoting of the front end of the handle around the top of a post 30 mounted on the barrel 1. As the handle rotates around the hinges 27 and 28, and slides on the post 30, the gate 20 slides between the closed and open positions. With the gate abutting a tree trunk, when pressure is applied to the handle 23, the various pieces of the latter rotate around the hinges 27 and 28 causing the gate to slide upwardly. Thus, the opening 21 is aligned with the open front end of the magazine 14 whereby a charge 16 can be pushed into the preformed recess in the tree by the spring 17.

The charge for inoculating and the type of material included within the inoculum (adjuvents) are important to the success of mycoherbicides. Each charge 16 is intended to introduce a biological herbicide, which has been proven to be effective, past the outer protective layers of a tree, and to provide a nutrient base from which the pathogen can initiate growth and colonize the weed tree.

Certain microorganisms intended as biocontrol agents must have a sufficient nutrient base from which to colonize the target weed tree. Initially, the microbe must be maintained until it begins active growth and enzymes germane to the target tree substratum (wood, bark, sap) can be mobilized. Thereafter, a good nutrient base in the charge will enable inoculum to colonize host tissues quickly enough to outgrow potential secondary organisms. This will vary between zero amendments (i.e., wood block blank alone) and a wood blank infiltrated with nutrients and a variety of adjuvants, as with certain fastidious microorganisms such as *Phacidium gaultheriae*. Such additives or adjuvants serve various purposes as diverse as generating a microsite favorable to the particular microbe being used, countering the effects of host tissue oxidants, discouraging the growth of bacteria, chelating ions, inactivating chelating agents in other instances, adjusting pH, and discouraging incursions of insects.

From an industrial use basis, the charge 16 must be durable, packaged for uncomplicated use by forest laborers who will install them, and they must yield consistent results. Consequently, a solid pellet loaded into a hard-walled, lightweight tubular plastic magazine 14, many of which can be slung in a quiver or pack, with the magazine loaded directly into the barrel 1 or a similar tool, is the ideal medium for tree inoculation. Dried, lyophilized charges are the ideal answers. However, not all fungi will survive that treatment. Consequently, an alternative is presented which will prove effective providing the charges are used promptly.

The charge 16 must yield consistent results and must be at least nearly equivalent to chemical herbicides in cost effectiveness. The charge 16 is produced from a 1.25 cm diameter dowel rod of straight-grain wood, e.g. Alder or Douglas fir, silica gel, clay, or other porous substance, bonded with a minimum of non-mycotoxic resin in the latter two instances, and formed with a jig to produce 2.54 cm length pieces. The pieces are tapered to yield a semi-rounded nose at either end upon a single application of the jig yielding a bland.

The blanks are twice-sterilized (24 hr interval between sterilizations) at approximately 15 PSI and 240° F. in an autoclave or similar pressure-heat device, maintained aseptic in a container upon removal and transferred to a freeze dryer (lyophilizer), where residual moisture is evacuated under vacuum. Thereafter, sterile liquid nutrient medium appropriate to the fungus to be incubated is introduced aseptically into the evacuated chamber. The medium may be altered with an antioxidant chemical if the target tree species produces oxidizing chemicals in large quantities, anti-bacterial chemicals if the potential use of requires such, and other adjuvants affecting the net growth or infection success of the intended mycoherbicide as required. Air is then admitted through a bacteria exclusion filter and the infiltrated blanks are give 24 hours to absorb the nutrient-adjuvant fluid mixture. Thereafter, a suspension of spores or comminuted mycelium (as appropriate) of the fungus pathogen intended for use is distributed over the surface of the infiltrated blanks, and the fungus is permitted to grow and colonize the blanks for an appropriate period and at an appropriate temperature (usually 60–90 days at 20° C.). The resultant mycoherbicide-colonized blanks are treated in one of two ways:

(1) The infiltrated pieces are surface-dried, coated with presterilized beeswax, and the wax is permitted to harden. The finished charges are loaded into gas-sterilized (with ethylene or propylene oxides) hardened plastic sleeves having internal diameters of 2.75 cm (the magazines 14), capped at both ends, and shipped for use within one week. The magazines 14 are manufactured for insertion in the barrel behind the gate 20. The inoculation opening in the tree has been closed with non-fungitoxic material in preliminary tests, which may or may not be necessary.

(2) The infiltrated pieces are relyophilized, coated with a sugar-soy mixture with final consistency similar to that of peanut brittle, allowed to harden, tumbled sufficiently to polish the surfaces of the pieces, then loaded into magazines 14 as above. These pieces are intended for long term storage.

I claim:

1. A biological method of controlling red alder tree comprising the step of injecting a cylindrical charge containing *Nectria ditissima* ATCC 74260 into the tree.

2. The method according to claim 1, wherein said *Nectria ditissima* ATCC 74260 is capable of killing the tree over a period of several years.

3. The method according to claim 1, wherein said charge has been impregnated with nutrients suitable for growing *Nectria ditissima* ATCC 74260 and wherein said *Nectria ditissima* ATCC 74260 is allowed to grow for two to three months on said charge before injecting said charge into a tree.

4. The method according to claim 3, wherein said charge has tapered ends.

5. The method according to claim 4, wherein the charge is a dowel rod of alder or douglas fir, or silica gel or clay bonded with a non-mycotoxic resin.

6. The method according to claim 5, wherein the charge is produced by forming a blank of said dowel rod, sterilizing said blank using heat and pressure, infiltrating the blank with a nutrient appropriate for the fungus *Nectria ditissima* ATCC 74260, distributing the fungus over the surface of the infiltrated blank, and permitting the fungus to grow for 60 to 90 days at 20° C.

7. The method according to claim 6, wherein the infiltrated blank is surface dried, coated with presterilized beeswax, and loaded into a gas-sterilized, hardened plastic sleeve for storage or shipping before use.

* * * * *